US007432308B2

(12) United States Patent
Demeester et al.

(10) Patent No.: US 7,432,308 B2
(45) Date of Patent: Oct. 7, 2008

(54) THERAPEUTIC COMPOSITIONS FOR THE TREATMENT OF A RESPIRATORY TRACT DISEASE

(75) Inventors: Joseph Demeester, Sint-Amandsberg (BE); Stefaan De Smedt, Mariakerke (BE); Niek Sanders, Erpe-Mere (BE)

(73) Assignee: Universiteit Gent, Gent (BE)

( * ) Notice: Subject to any disclaimer, the term of this patent is extended or adjusted under 35 U.S.C. 154(b) by 217 days.

(21) Appl. No.: 10/474,897

(22) PCT Filed: Apr. 15, 2002

(86) PCT No.: PCT/EP02/04198

§ 371 (c)(1),
(2), (4) Date: Feb. 17, 2004

(87) PCT Pub. No.: WO02/083167

PCT Pub. Date: Oct. 24, 2002

(65) Prior Publication Data

US 2004/0141961 A1 Jul. 22, 2004

(30) Foreign Application Priority Data

Apr. 13, 2001 (EP) .................................. 01201360

(51) Int. Cl.
*A61K 35/42* (2006.01)
*A61K 33/14* (2006.01)
*C12N 9/22* (2006.01)
*A01N 59/08* (2006.01)

(52) U.S. Cl. ........................ 514/851; 424/557; 424/681; 435/199

(58) Field of Classification Search .................. 424/557, 424/681; 514/851
See application file for complete search history.

(56) References Cited

U.S. PATENT DOCUMENTS 5,464,817 A * 11/1995 Stossel et al. ............... 514/2
5,985,339 A   11/1999 Kamarei

FOREIGN PATENT DOCUMENTS

| EP | 0406732 A2    | 1/1991  |
| EP | 0998945 A1    | 5/2000  |
| WO | WO 91/16909 A1 | 11/1991 |
| WO | WO 92/09290 A1 | 6/1992  |
| WO | WO 94/03189 A1 | 2/1994  |
| WO | WO 94/22465 A1 | 10/1994 |
| WO | WO 96/01627 A1 | 1/1996  |
| WO | WO 96/11016 A1 | 4/1996  |
| WO | WO 98/37096 A1 | 8/1998  |
| WO | WO 00/03746 A2 | 1/2000  |

OTHER PUBLICATIONS

Medline Plus Medical Encyclopedia: Asthma Oct. 27, 2004.*
Medline Plus Medical Encyclopedia: Lung disease Oct. 30, 2004.*
Medline Plus Medical Encyclopedia: Systemic lupus erythematosus Jul. 12, 2004.*
Shak et al. Proc. Natl. Acad. Sci. USA 1990, 87, 9188-9192.*
Campbell et al. The Journal of Biological Chemistry 1980, 255(8), 3726-3735.*
Pan et al. Biochemistry 1997, 36, 6624-6632.*
Prince et al. Clin. Exp. Immunol. 1998, 113, 289-296.*
Davis, et al. Lupus 1999, 8, 68-76.*
MedlinePlus Medical Encyclopedia: Cystic Fibrosis Jun. 8, 2005.*
MedlinePlus Medical Encyclopedia: Lung diseases Oct. 30, 2004.*
MedlinePlus Medical Encyclopedia: Mesothelioma Oct. 31, 2005.*
Dibbern DA. Wiskott-Aldrich Syndrome Jun. 10, 2005.*
MedlinePlus Medical Encyclopedia: Systemic lupus erythematosus Jul. 12, 2004.*
Akman et al. Autoimmune manifestations of the Wiskott-Aldrich Syndrome. Seminars in Arthritis and Rheumatism 1988, 27(4), 218-225.*
Shak et al. Aerosolized recombinant DNase I for the treatment of cystic fibrosis 1995, 107, 65-70.*
Shak et al. Recombinant human DNase I reduces the viscosity of cystic fibrosis sputum Proc. Nat. Acad. Sci. USA 1990, 87, 9188-9192.*
Campbell et al. The effect of divalent cations on the mode of action of DNase I. J. Biol. Chem. 1980, 225(8), 3726-3735.*
MedlinePlus Medical Encyclopedia: Asthma Oct. 27, 2004.*
Maruyama, "Effects of KC1, MgC12, and CaC12 Concentrations on the Monomer-Polymer Equilibrium of Actin in the PRescence and Absence of Cytochalasin D1", J. Biochemistry, vol. 96, No. 3, pp. 605-611, 1984.
Levy et al., "Bioactivity of Gentamicin in Purulent Sputum from Patients with Cystic Fibrosis or Bronchiectasis: Comparison with Activity in Serum," *The Journal of Infectious Diseases* 148(6): 1069-1076 (1983).

* cited by examiner

*Primary Examiner*—Johann Richter
*Assistant Examiner*—Ernst Arnold
(74) *Attorney, Agent, or Firm*—Clark & Elbing LLP

(57) ABSTRACT

The equilibrium between G actin and F actin is shifted towards the F actin confirmation with compounds such as the ionic form of magnesium or potassium. The higher amount of F actin decreases the inhibition of nucleases such as DNAse I by monomeric G actin. The increased performance of the nuclease results in better treatment of patients suffering from cystic fibrosis or other diseases with viscous mucus.

6 Claims, No Drawings

THERAPEUTIC COMPOSITIONS FOR THE TREATMENT OF A RESPIRATORY TRACT DISEASE

This application is a 371 of PCT/EP02/04198 filed on Apr. 15, 2002 and claims foreign priority to EPO 01201360.3 filed on Apr. 13, 2001.

The present invention describes a method to improve the performance of DNA degrading proteins (DNAse) in the treatment of pulmonary disease such as cystic fibrosis. The negative affect of actin monomers on the activity of DNAse is countered by shifting the equilibrium of actin towards it polymeric, filamentous state. This shift is performed by ions such as magnesium or potassium and are administered in a combination with DNAse.

BACKGROUND OF THE INVENTION

Cystic fibrosis (hereinafter referred as CF) is characterized by the presence of highly viscous pulmonary secretions in the lung (Wine in *J. Clin. Invest.* (1999) 103:309-312). The origin of these secretions, also described as mucus, which covers the epithelial cells of the bronchi and upper airways, has been associated with a mutation in the CFTR (i.e. Cystic Fibrosis Transmembrane conductance Regulator) gene (Collins in *Science* (1992) 256:774-779). CFTR codes for a protein, which functions as a chloride channel in the apical membrane of epithelial cells of the lung and intestine. In the lung this leads to a decreased chloride flux from the epithelial cells into the respiratory mucus layer. This, combined with an increased sodium and water absorption from the mucus into the cells (Knowles in *N. Engl. J. Med.* (1981) 305:1489-1495) probably results in an enhancement of the mucus viscoelasticity. Additionally, it is hypothesized that the gene defect in CF may also lead to altered mucins which bind bacteria more tightly (Scharfman et al. in *Infect Immun.* (1996) 64:5417-5420).

Due to the impaired clearance of inhaled pathogens, chronic bacterial colonization of the lungs are very common in CF patients. These lung infections evoke a migration of leukocytes and neutrophils into the mucus. However, these inflammatory cells, together with the pathogens and epithelial cells also die and release nuclear DNA and actin in the mucus, which further enhances the viscoelasticity and the decreased clearance of the mucus. DNA concentration in the mucus of CF patients typically ranges from 1-15 mg/ml (Shah et al. in *Respir. Med.* (1995) 89:499-502; Zahm et al. in *Eur. Respir. J.* (1995) 8:381-386; Vasconcellos et al. in *Science* (1994) 263:969-971; Sanders et al. in *Am. J. Respir. Crit. Care Med.* (2001) 164:486-493).). The high viscosity of mucus also causes suffering and even morbidity in diseases like chronic bronchitis, bronchiectasis, emphysema, acute and chronic sinusitis.

Some of the compounds in mucus (DNA and actin) are released from leukocytes that infiltrate pulmonary tissue in response to the presence of micro-organisms, such as *Pseudomonas, Pneumococcus* and *Staphyloccus* bacteria, or other irritating factors such as pollen and smoke.

In order to facilitate the removal of lung secretions, mucolytic drugs able to decrease the mucus viscoelasticity are often used. The viscosity of mucus of CF patients is significantly reduced by the administration of DNA degrading proteins. The protein most frequently used is DNAse I, an endonuclease that hydrolyses the highly viscous double stranded and single stranded DNA preferentially at a site adjacent to pyrimidine nucleotides, resulting in shorter oligonucleotides with decreased viscosity. In addition, surfactants in the sputum are released when the DNA network is degraded.

DNAse I has an optimal activity at a pH between about 5.5 and 7.5, preferably near pH 7.0 (Shak et al. (1990) Proc. Natl. Acad. Sci USA 87, 9188-9192). The presence of divalent cations, such as magnesium, in the catalytic centre of DNAse I is essential for its activity. In the presence of $Mg^{2+}$ the cleavage at both strands occurs independently from each other. In the presence of manganese ($Mn^{2+}$) ions, cleavage occurs at approximately the same site, resulting in blunt or nearly blunt ended fragments.

The human homologue of human DNAse I has been purified, cloned and expressed as a recombinant protein and is approved as a medicine. Recombinant human DNAse I (hereinafter rhDNAse I) is commercially available under the trade name Pulmozyme and is also designated as "dornase alpha". Although clinical trials have shown that rhDNAse I significantly improves lung function and decreases exacerbations in some CF patients (Shah et al. in *Respir. Med.* (2000) 89:499-502; Fuchs et al in *N. Engl. J. Med.* (1994) 331:637), it does not mean that all patients show clinical improvements. Indeed, other studies claim that there is a wide variation in clinical response of CF patients to rhDNAse I (in particular Bollert in *Eur. Respir. J.* (1999) 13:107-113; Christopher in *J. Clin. Pharm. Ther.* (1999) 24:415-426; Cobos in *Eur. J. Pediatr.* (2000) 159:176-181) and that a significant number of patients (the so-called non-responders) show no benefit from rhDNAse I therapy.

The reason for the failure in these non-responders is not clearly understood. Several variants or alternatives on the rhDNAse I treatment, some of them being relevant to the present invention, are described below.

The high viscosity of the mucus impedes the diffusion and penetration of DNAse inwards the mucus. Some surfactants that also reduce the viscosity may provide additional benefits by increasing the diffusion and subsequent performance of administered DNAse. U.S. Pat. No. 5,830,436 provides an example of an alkylaryl polyether alcohol polymer surfactant used in the treatment of pulmonary diseases.

DNAse I is subject to proteolytic degradation by proteases that are produced by leukocytes. The most predominant protease is elastase. U.S. Pat. No. 6,124,257 describes the administration of protease inhibitory proteins in order to improve the integrity and activity of DNAse I.

The catalytic activity of DNAse can be impeded by a shift in pH due to acidic compounds present in the mucus of patients, especially when pH shifts outside of the optimal pH range of 5.5-7.5. U.S. Pat. No. 5,863,563 describes the administration of a pH-raising buffer as a powder or as a nebulised solution. As a consequence of this buffering, DNAse I is able to perform in an optimal pH environment.

The activity of DNAse I decreases with time due to a chemical automodification of an aspartic acid into an isoaspartic acid. A purification method to remove the inactive modified DNAse I and an alternative storage method to prevent this modification are described in U.S. Pat. No. 5,783,433 and U.S. Pat. No. 5,279,823. Herein, the non-deamidated form of DNAse I is separated from the amidated form by ion exchange chromatography.

A major drawback in the DNAse I treatment of pulmonary diseases is its binding to monomeric actin and its subsequent inactivation. Pulmonary diseases are diseases which affect lung function. Such diseases may result from a defect in a gene or genes associated with lung function, asthma, allergies, an immune or an autoimmune disorder a microbial infection or a mechanical injury to the lungs. Actin is the most abundant protein in nucleated animal cells and constitutes approximately 10 to 20% of the protein of many nucleated cells and 30% of the protein of muscle cells. Actin molecules each bind an ATP (adenosine 5'-triphosphate) or ADP (adenosine 5'-diphosphate) molecule and self-assemble into long filaments during which the ATP is hydrolysed into ADP. Injury to animal tissues results in the release of actin into the extracellular space. Although approximately half of non-muscle cell actin is F-actin (the double-helical, rod-like, filament form of actin which is assembled from G-actin monomers). The ionic conditions of extracellular fluids are expected to favour actin polymerisation, so that virtually all the actin released from dying cells would polymerise into filaments if sufficiently concentrated (i.e. greater than a few micrograms per millilitre) as disclosed by Lind et al. in *Am. Rev. Respir. Dis.* (1988) 138:429-434). In purified solutions, in the absence of filament-shortening proteins, actin filaments can easily attain lengths of several microns. A wide variety of factors that influence the equilibrium between monomeric G-actin and polymeric F-actin are known. A non exhaustive list of these includes toxins (e.g. phalloidin), numerous proteins (lysozymes, kinases, actin related proteins, actin binding proteins) and a variety of ions (potassium, magnesium, cadmium, lithium, nickel, ammonium) as disclosed by Higgs et al. in *J. Biol. Chem.* (1999) 274:32531-4; Richard et al. in *Int. Microbiol.* (1999) 2:185-94; Sun et al in *Curr. Opin. Cell. Biol.* (1995) 7:102-110; Carlier et al. in *Adv. Exp. Med. Biol.* (1994) 358:71-81; Estes et al. in *Cell Motil.* (1992) 13:272-284; Shu et al. in *Biochem. J.* (1992) 283:567-573; Pollard in *Curr. Opin. Cell. Biol.* (1990) 2:33-40 and Korn in *Physiol. Rev.* (1982) 62:672-737. The interconversion from G actin to F actin is promoted by $Mg^{2+}$ and $K^+$ ions (Shu et al. in *Biochem. J.* (1992) 283:567-573). The differences in $K^+$ and $Mg^{2+}$ concentration in the two groups (i.e., responders and non responders on DNAse I) are relevant in terms of influencing the polymerisation state of actin. Maximal polymerisation is obtained with concentrations of 2 mM $Mg^{2+}$ or 200 mM K+ (Shu et al. cited supra).

Due to the large amounts of actin present in cells, the release of actin from dying cells provides sufficient actin to have a significant effect on the microenvironment by increasing the viscosity of extracellular fluids, such as mucus. The lysis of neutrophils is the major source of actin in the mucus of CF patients.

The therapeutic effect of DNAse I on the treatment of diseases such as CF has been attributed to the degradation of the DNA released by the neutrophils resulting in a decreased viscosity. The activity of DNAse I is strongly influenced by the presence of actin. DNAse I binds to G actin after which it is inactivated (Ulmer et al. in *Proc. Natl. Acad. Sci. USA* (1996) 93:8225-8229). As a consequence of the binding of DNAse I to the actin monomer, DNAse I also acts as an actin depolymerising compound according to Vasconcellos et al. in *Science* (1994) 263, 969-971. It was suggested that the mucolytic effect of DNAse in pulmonary secretions was rather to actin disaggregating than to DNA hydrolysis. Mutational analysis of DNAse I disproved this hypothesis (Ulmer et al. cited supra).

The inactivation of DNAse I due to the binding to G-actin is a major problem for the therapeutic use of DNAse I. Attempts to circumvent this problem have been made, especially by trying to decrease the DNAse actin interaction by using alternative forms of DNAse. Examples of such attempts are the use of site directed mutagenesis of DNAse I in order to decrease its binding affinity for actin (International patent publication WO 96/26279), the use of DNAse I having a lower pH optimum but which does not bind to actin (International patent publication WO98/16659) or the use of novel DNAse molecules having a lower affinity for actin (International patent publication WO97/28266).

As an alternative, the formation of free G actin is prevented by some actin binding proteins. For instance, U.S. Pat. No. 5,656,589 describes the administration of plasma gelsolin and vitamin D binding protein to patients with pulmonary diseases. Gelsolin has three actin binding sites and can bind to monomeric and polymeric actin. It therefore has as such a viscosity decreasing effect by severing actin filaments and has a beneficial effect on the DNAse I treatment by binding the inhibitory G actin before the latter binds to DNAse I. U.S. Pat. No. 5,464,817 describes the detrimental influence of contaminants associated with actin binding proteins, such as non-actin binding peptides, carbohydrates, glycosylated peptides, lipids, membranes and others. These contaminants can be harmful as such when administered together with the pharmaceutical compound or can interfere with the desired therapeutic effects.

Therefore there is a constant need in the art for improving the performance of DNAse I in the treatment of pulmonary diseases such as CF. Since most of the above-described solutions to this problem involve the administration of proteins which, as is well known to the skilled person, encounter stability problems and can provoke immune reactions, there is also a need for a more simple and less expensive solution to the above problem.

Other diseases are also concerned by an excess of G-actin or a decrease in intracellular F-actin. An example of such diseases is the Wiskott Aldrich Syndrome (hereinafter WAS) where a mutation in the X chromosome in the gene for WAS protein (hereinafter WASP) results in an X-linked hereditary disease characterised by thrombocytopenia with small platelet size, eczema, and increased susceptibility to infections and bloody diarrhoea. Death usually occurs before the age of 10 years according to Derry et al. in *Hum. Molec. Genet.* (1995) 4:1127-1135 and Derry et al. in *Cell* (1994) 78:635-644. The WASP protein was shown to regulate the intracellular actin network. Defective WASP results in a lower level of F-actin (Fachetti et al. in *J. Pathol.* (1998) 185:99-107; Gallego et al. in *Blood* (1997) 90:3089-3097). Therefore there is a need in the art for promoting F actin formation by shifting the equilibrium between G actin and F actin for the prevention or treatment of such diseases induced by or inducing an excess of G actin.

Systemic Lupus Erythematosus (SLE) is characterized by the production of pathogenic autoantibodies against nucleoprotein antigens and double stranded DNA (dsDNA). SLE is a multifactorial and polygenic disease. It is a chronic, remitting, relapsing, inflammatory, and often febrile multisystemic disorder of connective tissue, acute or insidious at onset, is characterized principally by involvement of the skin, joints, kidneys, and serosal membranes. Of unknown aetiology, lupus erythematosus is thought to represent a failure of the regulatory mechanisms of the autoimmune system. (see Online Mendelian Inheritance in Man, OMIM (TM) Johns Hopkins University (Baltimore, Md.) and National Center for Biotechnology Information, National Library of Medicine (Bethesda, Md.)).

In a lupus prone mouse model it has been shown that rhDNase I administration delays the development of dsDNA antibodies, reduces proteinuria and delays mortality. The pharmacokinetics and the activity of disease markers after administration of rhDNAse I were determined by Davis et al. in *Lupus* (1999) 8:68-76 and Prince et al. in *Clin. Exp. Immunol.* (1998) 113:289-296. These studies show that rhDNAse I is able to degrade DNA in DNA/antibody complexes and that inhibitors are present in the serum of patients.

The use of magnesium as a therapeutic agent has been reviewed by Swain et al. in *South Med. J.* (1999) 92:1040-1047. Magnesium has long been used as an ingredient in laxatives and antacids. Intravenous magnesium also is effective for the suppression of ventricular ectopy in the hospital setting and is a first-line agent for torsades de pointes. It is less clear whether it is useful in patients with congestive heart failure or acute myocardial infarction. Although effective for treatment of pre-eclampsia and eclampsia, its use in the termination of pre-term labor has recently been questioned. In asthma and chronic lung disease, intravenous magnesium may also be useful. Finally, magnesium may have a role in the prevention and treatment of vascular headaches.

In allergic diseases such as asthma, magnesium plays a role in the inhibition of histamine release from mast cells or in the relaxation of smooth lung muscle (Nannini et al. in *Chest* (1997) 111:858-861). In this respect, magnesium is not interfering with externally supplied therapeutic compounds.

SUMMARY OF THE INVENTION

A systematic survey of compounds present in sputum which might interfere with DNAse's such as DNAse I has not been performed until now. Analysis of the ionic content of mucus in CF patients is generally restricted to sodium and chlorine. No difference in other ion levels was seen between healthy persons and CF patients according to Noone et al. in *Chest* (1997) 112:1283-1290.

Based on such a systematic survey performed by the inventors, the present invention deals, in general terms and without being limited by theory, with influencing the actin polymerisation degree and modulating the inhibitory effect of G actin in the treatment of diseases induced by or inducing an excess of G-actin, for instance pulmonary diseases characterised by the presence of viscous mucus such as CF. Surprisingly, it was found that by shifting the actin toward its F-actin polymeric conformation, the positive effect of the improved DNAse I performance overrules the increased viscosity that is caused by the higher content of F-actin.

A first object of the present invention therefore is the use of a compound able to promote F actin formation by shifting the equilibrium between G actin and F actin for the treatment of a disease of the respiratory tract. The said use may be in the manufacture of a medicament. Vasconcellos et al. (cited supra) specifically teaches away from this finding.

A second object of the present invention is the use of a is one or more of an ionic form of potassium, magnesium, calcium, cadmium, nickel, manganese, cobalt, lithium, zinc, ammonium polyamine or macrocyclic polyammonium salt, preferably a potassium and/or magnesium salt for promoting F actin formation by shifting the equilibrium between G actin and F actin for the prevention or treatment of a disease induced by or inducing an excess of G actin. The said use may be in the manufacture of a medicament.

Another object of the present invention is a pharmaceutical composition for the treatment of a pulmonary disease characterised by the presence of viscous mucus, comprising:
(a) one or more compounds able to promote F actin formation by shifting the equilibrium between G actin and F actin, and
(b) a DNA degrading enzyme in respective proportions such as to provide a synergistic effect in the reduction of mucus viscosity, as a combined preparation for simultaneous, separate or sequential use. However it should be understood that compound (a) is not an excipient for DNAse.

Yet another object of the present invention is a method of treatment of a pulmonary disease characterised by the presence of viscous mucus in an animal, comprising administering to the animal in need of such treatment a therapeutically effective amount of:
(a) a compound able to promote F actin formation by shifting the equilibrium between G actin and F actin, and
(b) a DNA degrading enzyme in respective proportions such as to provide a synergistic effect in the reduction of mucus viscosity. The compound (a) and the DNA degrading enzyme (b) can be administered simultaneously, separately or sequentially. For instance compound (a) can be administered before the DNA degrading enzyme (b). The compound (a) is preferably an one or more inorganic salt which can be selected from potassium, magnesium, calcium, zinc, lithium, manganese, cadmium, nickel, cobalt, ammonium, polyamine and macrocyclic polyammonium salts. The DNA degrading enzyme can be a endonuclease, for example DNAse I.

Compound (a) can be selected from:

potassium chloride (KCl), potassium bromide (KBr), potassium iodide (KI), potassium fluoride (KF), potassium hydroxide (KOH), potassiumhexafluosilicate, potassium sulphates ($K_2SO4$, $KHSO_4$), potassium phosphates ($K_3PO_4$, $K_2HPO_4$, $KH_2PO4$), potassium carbonates ($K_2CO_2$, $KHCO_3$), potassium oxide ($K_2O$), ammonium potassium phosphates, potassium acetate ($K(CH_3COO)$), potassium citrate, potassium acetates, and other potassium salts, magnesium chloride ($MgCl_2$), magnesium bromide ($MgBr_2$), magnesium iodide ($MgI_2$), magnesium fluoride ($MgF_2$), magnesium hydroxide ($Mg(OH)_2$), magnesiumhexafluosilicate, magnesium sulphates (MgSO4, $Mg(HSO4)_2$, magnesium phosphates ($Mg_3(PO_4)_2$, $MgHPO_4$, $Mg(H_2PO4)_2$), magnesium carbonates ($MgCO_2$, $Mg(HCO_3)_2$), magnesium oxide (MgO), ammonium magnesium phosphates, magnesium acetate ($Mg(CH_3COO)_2$), magnesium citrate, magnesium acetates, and other magnesium salts, calcium chloride ($CaCl_2$), calcium bromide ($CaBr_2$), calcium iodide ($CaI_2$), calcium fluoride ($CaF_2$), calcium hydroxide ($Ca(OH)_2$), calciumhexafluosilicate, calcium sulphates (CaSO4, $Ca(HSO4)_2$), calcium phosphates ($Ca_3(PO_4)_2$, $CaHPO_4$, $Ca(H_2PO4)_2$), calcium carbonates ($CaCO_2$, $Ca(HCO_3)_2$), calcium oxide (CaO), ammonium calcium phosphates, calcium acetate ($Ca(CH_3COO)_2$), calcium citrate, calcium acetates, and other calcium salts, cadmium chloride ($CdCl_2$), cadmium bromide ($CdBr_2$), cadmium iodide ($CdI_2$), cadmium fluoride ($CdF_2$), cadmium hydroxide ($Cd(OH)_2$), cadmiumhexafluosilicate, cadmium sulphates (CdSO4, $Cd(HSO4)_2$), cadmium phosphates ($Cd_3(PO_4)_2$, $CdHPO_4$) $Cd(H_2PO4)_2$), cadmium Carbonates ($CdCO_2$, $Cd(HCO_3)_2$), cadmium oxide (CdO), ammonium cadmium phosphates, cadmium acetate ($Cd(CH_3COO)_2$), cadmium citrate, cadmium acetates, and other cadmium salts, ammonium chloride (($NH_4$)Cl), ammonium bromide (($NH_4$)Br), ammonium iodide (($NH_4$)I), ammonium fluoride (($NH_4$)F), ammonium hydroxide (($NH_4$)OH), ammoniumhexafluosilicate, ammonium sulphates (($NH_4$)$_2$SO4, ($NH_4$) HSO$_4$), ammonium phosphates (($NH_4$)$_3$PO$_4$, ($NH_4$)$_2$HPO$_4$) ($NH_4$)H$_2$PO$_4$), ammonium carbonates (($NH_4$)$_2$CO$_2$, (NH4) HCO$_3$), ammonium oxide ((NH4)$_2$O), ammonium acetate (($NH_4$)(CH$_3$COO)), ammonium citrate, ammonium acetates, and other ammonium salts, lithium chloride (LiCl), lithium bromide (LiBr), lithium iodide (LiI), lithium fluoride (LiF), lithium hydroxide (LiOH), lithiumhexafluosilicate, lithium sulphates ((Li)$_2$ SO4, LiHSO$_4$), lithium phosphates ((Li)$_3$PO$_4$, (Li)$_2$HPO$_4$) LiH$_2$PO$_4$), lithium carbonates ((Li)$_2$CO$_2$, LiHCO$_3$), lithium oxide ((Li)$_2$O), lithium acetate (Li(CH$_3$COO)), lithium citrate, lithium acetates, and other lithium salts, nickel chloride (NiCl$_2$), nickel bromide (NiBr$_2$), nickel iodide (NiI$_2$), nickel fluoride (NiF$_2$), nickel hydroxide (Ni(OH)$_2$), nickelhexafluosilcate, nickel sulphates (NiSO4, Ni(HSO4)$_2$), nickel phosphates ((Ni$_3$(PO$_4$)$_2$, NiHPO$_4$, Ni(H$_2$PO4)$_2$), nickel carbonates (NiCO$_2$, Ni(HCO$_3$)$_2$), nickel oxide (NiO), ammonium nickel phosphates, nickel acetate (Ni(CH$_3$COO)$_2$), nickel citrate, nickel acetates, and other nickel salts, zinc chloride (ZnCl$_2$), zinc bromide (ZnBr$_2$), zinc iodide (ZnI$_2$), zinc fluoride (ZnF$_2$), zinc hydroxide (Zn(OH)$_2$), zinchexafluosilicate, zinc sulphates (ZnSO4, Zn(HSO4)$_2$), zinc phosphates ((Zn$_3$(PO$_4$)$_2$, ZnHPO$_4$, Zn(H$_2$PO4)$_2$), zinc carbonates (ZnCO$_2$, Zn(HCO$_3$)$_2$), zinc oxide (ZnO), ammonium zinc phosphates, zinc acetate (Zn(CH$_3$COO)$_2$), zinc citrate, zinc acetates, and other zinc salts, manganese chloride (MnCl$_2$), manganese bromide (MnBr$_2$), manganese iodide (MnI2), manganese fluoride (MnF$_2$), manganese hydroxide (Mn(OH)$_2$), manganesehexafluosilicate, manganese sulphates (MnSO4, Mn(HSO4)$_2$, manganese phosphates (Mn$_3$(PO$_4$)$_2$, MnHPO$_4$, Mn(H$_2$PO4)$_2$), manganese carbonates (MnCO$_2$, Mn(HCO$_3$)$_2$), manganese oxide (MnO), ammonium manganese phosphates, manganese acetate (Mn(CH$_3$COO)$_2$), manganese citrate, manganese acetates, and other manganese salts, polyamine or macrocyclic polyammonium chloride, polyamine or macrocyclic polyammonium bromide, polyamine or macrocyclic polyammonium iodide, polyamine or macrocyclic polyammonium fluoride, polyamine or macrocyclic polyammonium hydroxide, polyamine or macrocyclic polyammoniumhexafluosilicate, polyamine or macrocyclic polyammonium sulphates, polyamine or macrocyclic polyammonium phosphates, polyamine or macrocyclic polyammonium carbonates, polyamine or macrocyclic polyammonium oxide, ammonium polyamine or macrocyclic polyammonium phosphates, polyamine or macrocyclic polyammonium acetate, polyamine or macrocyclic polyammonium citrate, polyamine or macrocyclic polyammonium acetates, and other polyamine or macrocyclic polyammonium salts, cobalt chloride (CoCl$_3$), cobalt bromide (CoBr$_3$), cobalt iodide (CoI$_3$), cobalt fluoride (CoF$_3$), cobalt hydroxide (Co(OH)$_3$), cobalthexafluosilicate, cobalt sulphates (CO$_2$(SO$_4$)$_3$, Co(HSO4)$_3$, cobalt phosphates (CoPO$_4$, Co$_2$(HPO$_4$)$_3$) Co(H$_2$PO4)$_3$, cobalt carbonates (Co2(CO$_2$)$_3$, Co(HCO$_3$)$_3$), cobalt oxide (Co$_2$O$_3$), ammonium cobalt phosphates, cobalt acetate (Co(CH$_3$COO)$_3$), cobalt citrate, cobalt acetates, and other cobalt salts.

The above method may be used for the treatment of cystic fibrosis. Another aspect of the present invention is the assessment of the suitability of the therapeutic compositions of the present invention for a patient suffering from pulmonary disease characterised by the presence of viscous mucus The attached claims define further embodiments of the present invention.

DETAILED DESCRIPTION OF THE INVENTION

Definitions

"disease of the respiratory tract" in the present invention refers to a disease which affects the air passages from nose to pulmonary alveoli through pharynx, larynx, trachea and bronchi and which affects lung function. Such conditions may result from a defect in a gene or genes associated with lung function (e.g., cystic fibrosis), asthma, allergies, an immune or autoimmune disorder, a microbial infection (e.g. bacterial, viral, fungal or parasitic infection), or a mechanical injury to the lungs.

"pulmonary disease characterised by the presence of viscous mucus" in the present invention refers to diseases such as cystic fibrosis, chronic bronchitis, bronchiectasis, emphysema, acute and chronic sinusitis.

"cystic fibrosis" is a congenital metabolic disorder [OMIM 219700] in which secretions of exocrine glands are abnormal; excessive viscous mucus causes obstruction of passage ways (including pancreatic and bile ducts, intestines and bronchi), and the sodium and chloride content of sweat are increased throughout the patient's life; symptoms usually appear in childhood and include meconium ileus, poor growth despite good appetite, malabsorption and foul bulky stools, chronic bronchitis with cough, recurrent pneumonia, bronchiectasis, emphysema, clubbing of the fingers and salt depletion in hot weather. The disease is caused by a mutation in the CFTR gene (Cystic Fibrosis Transmembrane conductance Regulator) located on chromosome 7q. Cystic fibrosis s also known as mucoviscidosis.

"DNAse", "nuclease", or "DNA degrading enzyme" all relate to enzymes which catalyze the hydrolysis of double stranded or single stranded nucleic acids into nucleotides or oligonucleotides by cleaving phosphodiester linkages. They can be endonucleases, cleaving internal phosphodiester linkages, or exonucleases, nucleases that release one nucleotide, serially at a time, beginning at one end of a polynucleotide (5' or 3', or both).

Methods to improve the efficiency of the DNAse I treatment of patients suffering from pulmonary disease such as CF are usually intended to reduce the viscoelasticity of mucus by (i) increasing the performance of DNAse I, (ii) preventing the binding of DNAse I to G actin and (iii) using G actin binding proteins. This invention exploits the physicochemical behaviour of actin not by preventing the inactivation of DNAse I or by using compounds that bind G actin, but by promoting the formation of F actin.

It is known from the prior art that ions like magnesium and potassium have an influence on the polymerisation of actin. By supplementing these ions to the mucus of patients according to the present invention, the equilibrium of actin polymerisation is shifted towards the F actin conformation. On the one hand, as a consequence the inhibition of DNAse I activity by binding to monomeric G-actin is strongly reduced. On the other hand, the viscosity of the mucus is expected to increase due to the higher viscoelasticity of the larger proportion of F-actin as compared to non-supplemented mucus. In particular, a good correlation is shown between the concentration of potassium and magnesium ions present in the sputum of patients and the reduction in viscoelasticity after DNAse I treatment. This results in the more general teaching of using a one or more compounds able to promote F actin formation by shifting the equilibrium between G actin and F actin for the treatment of a disease of the respiratory tract. Preferably, the said compound:

- is a potassium, magnesium, calcium, cadmium, nickel, manganese, cobalt, lithium, zinc, ammonium polyamine or macrocyclic polyammonium salt.
- is used in combination with DNAse I or another suitable nuclease.

Preferably in the latter case, the promotion of F actin formation is effected before G actin binds to DNAse I. Also preferably, the disease to be treated is a pulmonary disease characterised by the presence of viscous mucus, such as cystic fibrosis.

The concentration of the salt composition which is supplied to the patient by means such as the nebulisation of an aerosol should be sufficiently high to obtain the desired concentration of salt in the respiratory sputum of the patient. For example, the concentration of $Mg^{2+}$ in an aerosol should be sufficiently high to obtain in the respiratory mucus a concentration of magnesium ions of at least 2 mM, preferably between 5 and 500 mM more preferable between 20 and 100 mM. In order to achieve this the concentration of magnesium ions in the aerosol is preferably between 5 and 5000 mM, more preferably between 20 and 100 mM. For example, the concentration of $K^+$ ions in an aerosol should be sufficiently high to obtain in the respiratory mucus a concentration of potassium ions of at least 15 mM, preferably between 15 and 5000 mM more preferable between 20 and 100 mM. In order to achieve this the concentration of potassium ions in the aerosol is preferably between 50 and 3000 mM, more preferably between 20 and 500 mM.

As used herein, the term "DNAse I" refers to recombinant human DNAse I, as well as to native human DNAse I, as well as other DNAse I peptides which are compatible with human patients, along with synthetic DNAse I and biologically active abbreviated sequences, and biologically active analogues including mutants having substituted, deleted, elongated, replaced, or other modified sequences which posses bioactivity similar to that of DNAse I. As used herein, the term "salt" means a pharmaceutically acceptable grade of one or more mineral or organic salts of potassium, magnesium, calcium, cadmium, nickel, manganese, cobalt, lithium, zinc, ammonium polyamine or macrocyclic polyammonium in which the cation is associated with a suitable anion, as is well known in the art.

Another teaching of this invention is the use of a potassium and/or magnesium salt for promoting F actin formation by shifting the equilibrium between G actin and F actin for the prevention or treatment of a disease induced by an excess of G actin. An example of such disease, in addition to the previously mentioned pulmonary disease, is the Wiskott Aldrich Syndrome.

Another teaching of the invention is to improve the activity of a nuclease such as rhDNAse I in the treatment of LSE, the administration of magnesium and/or potassium salts can diminish eventual inhibition by G-actin.

The present invention also considers the application of magnesium and/or potassium salts in a combination with pomades containing a nuclease, such as rhDNAse I (Fibrinolysin W/Dnase, Elase, Fibrinolysin and Desoxyribonuclease topical). These pomades are used as a medicine for the removal of dead skin and tissue healing of wounds such as burns, ulcers, surgical wounds, circumcision or episiotomy.

Another teaching of this invention is the use of one or more potassium, magnesium calcium, cadmium, nickel, manganese, zinc, cobalt, lithium, ammonium polyamine or macrocyclic polyammonium salts for the manufacture of a medicament for the treatment of a pulmonary disease characterised by the presence of viscous mucus such as cystic fibrosis.

This invention also considers a pharmaceutical composition for the treatment of a pulmonary disease characterised by the presence of viscous mucus, comprising (a) one or more compounds able to promote F actin formation by shifting the equilibrium between G actin and F actin, and (b) a DNA degrading enzyme in respective proportions such as to provide a synergistic effect in the reduction of mucus viscosity, as a combined preparation for simultaneous, separate or sequential use. In this pharmaceutical composition:

- compound (a) is selected from potassium, magnesium, calcium, cadmium, nickel, manganese, cobalt, lithium, zinc, ammonium polyamine or macrocyclic polyammonium salts preferably selected from potassium and magnesium salts, more preferably, potassium hydrogenophosphate $K_2HPO_4$ and magnesium chloride $MgCl_2$.
- alternatively, compound (a) can be a compound leading to an increased potassium or magnesium concentration in mucus such as deoxycholic acid or odorants (e.g. butanol). Deoxycholic acid concentration of 0.5 mM are sufficient to stimulate $K^+$ secretion from epithelial cells into the mucus (Farack et al. (1982) *Naunyn Schmiedeberg Arch. Pharmacol.* 321,336-340. Also pharmaceutical compositions like potassium channels openers (for example Nicorandil) and calcium antagonists (for example Isotopine) can enhance respectively potassium and calcium ion concentrations.
- Alternatively, compound (a) can be a compound leading to an increased polymerisation of G actin in mucus such as ATP (adenosine 5' triphosphate), CAP III, Lipocortin-85, actin related protein 2, actin related protein 3, lyophaphatidic acid, oxytocin, recombinant Gcs1p, LIM kinases, WASP proteins, Rho family GTP ases FH family proteins, VASP proteins, 5'-3-O-(thio)triphosphate (GTP gamma S), profilin, phalloidin, lysozyme, Arg-Gly-Asp tripeptide, Arg-Gly-Asp tripeptide containing peptides, CapZ, tropomodulin, phorbol esters, retinoids, surfactants protein fragmin, surfactant proteins A and D.
- the DNA degrading enzyme preferably is a nuclease such as DNAse I or a variant thereof.

Preferably the pharmaceutical composition is intended for the treatment of cystic fibrosis. As readily understood by the skilled person, the amounts of active ingredients (a) and (b) in the composition are mucous viscosity reducing amounts. As usual in the art, the pharmaceutical, composition of the invention may further comprise at least a pharmaceutically acceptable carrier.

The term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders. More preferably however, the pharmaceutically acceptable carrier should be selected in such a way that the pharmaceutical composition of the invention can be inhaled.

Suitable pharmaceutical carriers for use in the pharmaceutical compositions of the invention are described for instance in Remington's Pharmaceutical Sciences 16 ed. (1980) and their formulation is well known to those skilled in the art. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the active ingredient in the composition. Controlled release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate muco adhesive polymers and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition comprising the active ingredient may be in a solid form such as a tablet and may require a protective coating. The pharmaceutical form suitable for injectionable use include sterile aqueous solutions or dispersions and sterile powders for the extemporaneous preparation thereof. Typical carriers therefore include biocompatible aqueous buffers, ethanol, glycerol, propylene glycol, polyethylene glycol and mixtures thereof.

The present invention also contemplates a method of treatment of a pulmonary disease characterised by the presence of viscous mucus in an animal, comprising administering to the animal in need of such treatment a therapeutically effective amount of (a) one or more compounds able to promote F actin formation by shifting the equilibrium between G actin and F actin, and (b) a DNA degrading enzyme in respective proportions such as to provide a synergistic effect in the reduction of mucus viscosity. In this method of treatment, the compound (a) and the DNA degrading enzyme (b) may be administered simultaneously, separately or sequentially. Preferably however, compound (a) is administered before the DNA degrading enzyme (b). In this method of treatment, which is preferably intended for the treatment of cystic fibrosis:

compound (a) is selected from potassium, magnesium, calcium, cadmium, nickel, manganese, cobalt, lithium, zinc, ammonium polyamine or macrocyclic polyammonium salts, preferably selected from potassium and magnesium salts, more preferably selected from potassium hydrogenophosphate $K_2HPO_4$ and magnesium chloride $MgCl_2$.

alternatively, compound (a) can be a compound leading to an increased potassium or magnesium concentration in mucus such as deoxycholic acid or odorants (e.g. butanol)

the DNA degrading enzyme preferably is a nuclease, more preferably DNAse I or a variant thereof.

The animal to be treated according to this method preferably is a human being.

The method is not restricted to the administration of rhDNAse I and cations such potassium and/or magnesium cations solely. Such cations can be supplied in any therapy where it is the aim of improving performance of DNA degrading enzymes. The invention therefore relates to any therapy wherein a DNAse (rhDNAse I or any other DNA degrading enzyme) is used.

The pharmaceutically active ingredients can be administered directly to the airways of the animal to be treated as a dry inhalable powder. The powder particles have preferentially a diameter not above 10 µm and may further include an additional compound compatible for inhalation. This additional compound can dilute the active ingredient, assist in a homogeneous distribution or prevent agglomeration, caking, or crystal growth. The additional compound can be, but is not limited to, lactose, maltose, xylitol, sorbitan trioleate, oleic acid or the like.

The pharmaceutical active ingredient can also be administered by the nebulisation of a solution. In this case, it is diluted in a compatible stabilising and buffering solution which may further contain carriers like droplet stabilising compounds, antifoaming agents, dispersing agents and/or other additives commonly used in this kind of formulation.

A variety of devices for the administration of liquids or powders is described and well known to those skilled in the art.

In some instances, it may assist in the efficiency of the therapy if the salt such as magnesium or potassium salt is orally supplied to the patient in the form of tablets.

The success of DNAse I therapy is not guaranteed and the therapy is expensive. Based on the findings described herein, an assay is developed to predict the success rate and to assess the suitability of DNAse I therapy in general and of the method of treatment of the invention (including the supplementation of salts such as magnesium or potassium salts) in particular. In a typical procedure, the $Mg^{2+}$ and/or $K^+$ content and the rheological parameters of the sputum of a patient are measured as described below. The sample is divided in fractions. A therapeutic amount of the said cation(s) is supplied to one fraction, after which the DNA of the samples is digested with rhDNAse I. After incubation, the digest is stopped by the addition of ethylenediamine tetraacetic acid (EDTA) and heating the samples for 20 minutes at 65° C. DNA is extracted by phenol/chloroform extraction or by any commercially available kit able to extract DNA from crude samples. Degradation of DNA is then evaluated by means of agarose gel electrophoresis. As a control, samples with and without supplemented ions are incubated in the absence of DNAse I.

G actin of sputum can be measured by adding sputum to a dilution series of DNAse with equal amounts of plasmid DNA. The presence of non degraded plasmid DNA after digestion is a parameter for G actin inactivating the DNAse.

Alternatively the presence of G actin in a sample and the consequences thereof on the activity of DNAse can be evaluated by adding one or more compounds which influence the actin polymerisation. Such compounds are for example, DNAseI itself, ATP (adenosine 5' triphosphate), CAP III, Lipocortin-85, actin related protein 2, actin related protein 3, lyophaphatidic acid, oxytocin, recombinant Gcs1p, LIM kinases, WASP proteins, Rho family GTP ases FH family proteins, VASP proteins, 5'-3-O-(thio)triphosphate (GTP gamma S), profilin, phalloidin, lysozyme, Arg-Gly-Asp tripeptide, Arg-Gly-Asp tripeptide containing peptides, CapZ, tropomodulin, phorbol esters, retinoids, surfactants protein fragmin, surfactant proteins A and D. The potential toxicity of these compounds is not relevant for these in vitro tests and makes them suitable for such diagnostics. Alternatively or in addition to said compounds one or more of the salts of potassium, magnesium, calcium, cadmium, nickel, manganese, cobalt, lithium, zinc, ammonium polyamine or macrocyclic polyammonium salt can be added.

Phalloidin binds specifically to F-actin. Fluorescent forms of phalloidin or coupled antibodies to phalloidin can be used as to demonstrate and quantify F-actin, and therefor indirectly the amount of G actin.

Characteristics related to the amount of G actin are features such as changes in viscosity and/or elasticity of a sample or changes in the concentration of degraded DNA by the activity of endogenous or added DNA.

The following examples are provided for illustrative purpose only and without any limiting intention.

EXAMPLE 1

Biochemical and Biophysical Characterisation of Sputum

Sputum was collected from CF patients in accordance with the rules of the Ethic Committee of the Universitary Hospital of Ghent, Belgium.

DNA and mucin concentration were measured according to Sanders et al. in *Am. J. Respir. Crit. Care Med.* (2000) 162:1905-1911. The osmolarity was determined using an advanced cryomatic osmometer Model 3C2 (Advanced Instruments, Needhamhigh, Mass.). Sodium, potassium and chloride concentrations were determined using ion selective electrodes. Concentrations of calcium (Ehrhardt et al. in *Wien. Klin. Wschr.* (1992) 104:5-11), magnesium (Ehrhardt et al. in *Wien. Klin. Wschr.* (1992) 104:5-11), inorganic phosphate (Fiske et al. in *J. Biol. Chem.* (1925) 66:375-400), bicarbonate (Peled in Methods of enzymatic analysis, 3rd edition (1985) (7) 572-577), phospholipid (Michelson in *Anal. Chem.* (1977) 29:60-65), protein (Weichselbaum in *Am. J. clin. Path.* (1946) 16:40-4), cholesterol (Roeschlau et al. in *J. Clin. Chem. Clin. Biochem.* (1974) 12:226-227) and triglyceride (Wahlefeld et al. in Methods of enzymatic analysis, 2nd English edition, Verlag Chemie (1974) (4) 1831) were measured. For all these assays we incubated 150 µl of CF sputum with 150 µl of 6 mM DTT (dithiothreitol), 100 mM sodium phosphate buffer pH 7.0 at 24° C. for 1 hour. DTT reduces the disulfide bridges in mucin, liquifies the sputum sample, and consequently facilitates sample manipulation. As a control was used 150 µl of distilled water with 150 µl of the buffered DTT solution. All these determinations (except the estimation of DNA, mucin and osmolarity) were performed using an automatic Hitachi 747 auto-analyser (Hitachi, Tokyo, Japan).

The experimental results are expressed as mean±standard deviation. As the number of data in each group was less than 30, the Mann-Whitney test was used to evaluate whether sputum from responders and non-responders showed a significant difference in the concentration of the analysed components. The Mann-Whitney test was also used to compare elasticity (G') and viscosity (G") of the sputum fractions before and after treatment with rhDNase I and to determine whether CF sputa which were degraded by rhDNase I in vitro showed significant differences in biochemical composition compared with CF sputa which were not degraded by rhDNase I in vitro. Significance was set at p=0.05.

The biochemical composition of the CF sputa of both responders and non-responders is shown in table 1 below, wherein * indicates that data are not available due to limited amounts of sample. Statistical analysis revealed that CF sputa which showed a decrease in viscoelasticity in vitro by rhDNase I had a significant higher osmolarity (p=0.02), DNA (p=0.03), protein (p=0.01), cholesterol (p=0.04), triglyceride (p=0.01), $K^+$ (p=0.02) and total magnesium (p=0.01) concentration. The higher DNA, protein, cholesterol and triglyceride concentrations of these sputa indicate that they were obtained from CF patients with more serious lung infections. As rhDNase I decreases viscoelasticity cleaving DNA, it was expected that sputa with high DNA concentrations showed also a decrease in viscoelasticty by rhDNase I in vitro.

Responders and non-responders had respectively in their sputum a mean total actin concentration of 0.06±0.01 mg/ml and 0.08±0.01 mg/ml.

Of the several parameters that were determined, only potassium and magnesium have a significantly higher concentration in the responder group (patients 1-13) compared to the non-responder group (patients 14-22) (p=0.04 and 0.02 respectively). In the responder group also a higher, although not significant, DNA concentration was observed (p=0.40). All non-responders had in their sputum a potassium concentration below 19.5 mM or a magnesium concentration below 1.4 mM. This correlation can be used as a parameter for predicting the response of CF patients on rhDNase I treatment.

The significant higher potassium and magnesium concentrations measured in the CF sputa obtained from responders and in sputa which are mucolysed by rhDNase I in vitro can explain the failure of treatment in non responders. The lower presence of $Mg^{2+}$ and $K^+$ in the non-responder group indeed promotes the G actin conformation that will result in a higher inactivation of DNAse I compared to the responder group. Besides the concentrations of these ions, the total actin content determines the concentration of G actin as well.

TABLE 1

| Patients | sputum sample | start value G' (Pa) | Start value G" (Pa) | osmolarity (mosmol) | $Na^+$ (mM) | $Cl^-$ (mM) | $K^+$ (mM) | total calcium (mM) | total magnesium (mM) | inorganic phosphate (mM) |
|---|---|---|---|---|---|---|---|---|---|---|
| responders | 1 | 25 ± 7 | 6.5 ± 1.3 | 250 | 79 | 64 | 21.7 | 2.9 | * | 20 |
| | 2 | 5.3 ± 0.8 | 2.1 ± 0.3 | 220 | 77 | 68 | 20.1 | 2.7 | * | 12 |
| | 3 | 14 ± 6 | 4.3 ± 1.5 | 276 | 109 | 88 | 16.6 | 1.9 | * | 15 |
| | 4 | 3.0 ± 0.4 | 1.2 ± 0.1 | 262 | 81 | 84 | 20.4 | 1.7 | * | 5 |
| | 5 | 16 ± 4 | 4.2 ± 0.9 | 238 | 77 | 66 | 23.5 | 2.5 | * | 26 |
| | 6 | 3.4 ± 0.8 | 1.4 ± 0.2 | 227 ± 7 | 85 ± 3 | 70 ± 1 | 17.5 ± 0.2 | 3.5 ± 0.3 | 1.5 ± 0.1 | 26 ± 3 |
| | 7 | 14 ± 4 | 3.3 ± 0.8 | 303 ± 18 | 83 ± 2 | 62 ± 1 | 20.8 ± 0.9 | 3.5 ± 0.2 | 2.7 ± 0.3 | 8 ± 1 |
| | 8 | 6.6 ± 0.6 | 2.7 ± 0.3 | 315 | 112 | 128 | 25.5 | 4.5 | 2.3 | 5 |
| | 9 | 4.0 ± 0.1 | 1.5 ± 0.1 | 296 ± 8 | 97 ± 5 | 119 ± 2 | 26.2 ± 1.5 | 2.7 ± 0.9 | 2.1 ± 0.2 | 7 ± 2 |
| | 10 | 2.8 ± 0.8 | 0.9 ± 0.1 | 203 ± 3 | 84 ± 2 | 75 ± 1 | 22.8 ± 0.4 | 3.0 ± 0.2 | 1.2 ± 0.2 | 14 ± 1 |
| | 11 | 10 ± 1 | 2.8 ± 0.5 | 251 ± 3 | 104 ± 2 | 86 ± 1 | 21.9 ± 0.1 | 3.3 ± 0.1 | 1.5 ± 0.1 | — |
| | 12 | 2.1 ± 0.2 | 1.2 ± 0.2 | 258 ± 1 | 104 ± 4 | 86 ± 2 | 18.4 ± 0.7 | 3.6 ± 0.3 | 1.8 ± 0.3 | 20 |
| | 13 | 3.7 ± 0.4 | 1.6 ± 0.1 | 288 ± 2 | 95 ± 1 | 74 ± 1 | 23.8 ± 0.1 | 4.7 ± 0.1 | 2.7 ± 0.1 | 26 ± 8 |
| mean | | 8 ± 7 | 3 ± 2 | 261 ± 34 | 91 ± 13 | 82 ± 20 | 21 ± 3 | 3.1 ± 0.9 | 2.0 ± 0.6 | 14 ± 9 |

| patient | sputum sample | bicarbonate (mM) | proteins (g/100 mL) | phospholipids (mg/100 mL) | cholesterol (mg/100 mL) | triglycerides (mg/100 mL) | DNA (mg/mL) | mucin (mg/mL) |
|---|---|---|---|---|---|---|---|---|
| responders | 1 | 19 | 3.9 | 346 | 170 | 134 | 7.4 ± 0.4 | * |
| | 2 | 10 | 1.5 | 114 | 48 | 36 | 2.39 ± 0.04 | * |
| | 3 | 5 | 1.3 | 80 | 36 | 46 | 2.3 ± 0.1 | * |
| | 4 | 4 | 0.5 | 50 | 30 | 26 | 1.5 ± 0.1 | * |
| | 5 | 15 | 2.9 | 312 | 148 | 108 | 4.8 ± 0.6 | * |
| | 6 | 13 ± 3 | 2.7 ± 0.8 | * | 167 ± 38 | 115 ± 18 | 2.7 ± 0.5 | 20 |
| | 7 | 21 ± 2 | 5.5 ± 0.6 | * | 269 ± 12 | 156 ± 7 | 4.1 ± 1.7 | 20 ± 5 |
| | 8 | 18 | 3.9 | * | 224 | 136 | 3.4 ± 0.3 | 32 ± 4 |
| | 9 | 12 ± 1 | 7 ± 1 | * | 211 ± 30 | 126 ± 10 | 4.2 ± 1.4 | 21 ± 2 |
| | 10 | 6 ± 1 | 1.3 ± 0.3 | * | 81 ± 20 | 45 ± 12 | 1.38 ± 0.02 | 8.9 ± 0.1 |
| | 11 | 4 ± 2 | 2.0 ± 0.2 | * | 72 ± 22 | 82 ± 18 | 1.2 ± 0.3 | 16 ± 3 |
| | 12 | 13 ± 2 | 2.6 ± 0.5 | * | 137 ± 56 | 92 ± 24 | 3.1 ± 0.1 | 11 ± 2 |
| | 13 | 21 ± 1 | 4.2 ± 0.1 | * | 247 ± 20 | 168 ± 20 | 4.1 0.3 | 18 ± 7 |
| mean | | 12 ± 6 | 3 ± 2 | 180 ± 138 | 142 ± 82 | 98 ± 47 | 3 ± 2 | 18 ± 7 |

| patient | sputum sample | start value G' (Pa) | Start value G" (Pa) | osmolarity (mosmol) | $Na^+$ (mM) | $Cl^-$ (mM) | $K^+$ (mM) | total calcium (mM) | total magnesium (mM) | inorganic phosphate (mM) |
|---|---|---|---|---|---|---|---|---|---|---|
| non-responders | 14 | 3.8 ± 0.7 | 1.4 ± 0.2 | 232 | 79 | 68 | 21.9 | 2.3 | * | 13 |
| | 15 | 17* | 4.0* | 224 | 67 | 58 | 18.5 | 3.6 | * | 11 |
| | 16 | 3.6 ± 0.1 | 1.5 ± 0.1 | 406 | 115 | 106 | 13.5 | 2.6 | * | 9 |
| | 17 | 11 ± 2 | 3.0 ± 0.5 | 228 ± 5 | 92 ± 7 | 75 ± 2 | 22.9 ± 0.7 | 2.2 ± 0.1 | 1.1 ± 0.1 | 13 ± 1 |
| | 18 | 7 ± 1 | 2.2 ± 0.2 | 268 ± 2 | 121 ± 1 | 103 ± 1 | 16.8 ± 0.3 | 3.0 ± 0.2 | 1.3 ± 0.1 | 16 ± 2 |
| | 19 | 2.5 ± 0.1 | 0.9 ± 0.1 | 231 ± 5 | 84 ± 2 | 71 ± 2 | 18.1 ± 0.3 | 3.6 ± 0.2 | 1.7 ± 0.1 | 12 ± 3 |
| | 20 | 2.1 ± 0.3 | 1.0 ± 0.1 | 231 ± 2 | 96 ± 1 | 89 ± 1 | 18.4 ± 0.1 | 3.0 ± 0.1 | 1.2 ± 0.1 | 12 ± 5 |
| | 21 | 6 ± 1 | 1.9 ± 0.4 | 191 ± 3 | 85 ± 3 | 73 ± 2 | 15.2 ± 0.2 | 2.5 ± 0.2 | 1.0 ± 0.1 | 6 ± 4 |
| | 22 | 8 ± 2 | 2.1 ± 0.5 | 226 ± 4 | 92 ± 5 | 76 ± 2 | 18.1 ± 0.5 | 3.2 ± 0.3 | 1.4 ± 0.2 | 2 ± 1 |
| mean | | 7 ± 5 | 2 ± 1 | 249 ± 62 | 92 ± 17 | 80 ± 16 | 18 ± 3 | 2.9 ± 0.5 | 1.3 ± 0.3 | 11 ± 4 |

| Patient | sputum sample | bicarbonate (mM) | proteins (g/100 mL) | phospholipids (mg/100 mL) | cholesterol (mg/100 mL) | triglycerides (mg/100 mL) | DNA (mg/mL) | mucin (mg/mL) |
|---|---|---|---|---|---|---|---|---|
| non-responders | 14 | 10 | 2.9 | 270 | 78 | 106 | 3.2 ± 0.4 | * |
| | 15 | 15 | 3.3 | 302 | 176 | 118 | 4.9 ± 0.5 | * |
| | 16 | 5 | 1.1 | 70 | 38 | 54 | 1.48 ± 0.04 | * |
| | 17 | 9 ± 2 | 2.1 ± 0.1 | * | 72 ± 2 | 32 ± 11 | 2.2 ± 0.5 | 11 ± 5 |
| | 18 | 5 ± 1 | 1.7 ± 0.4 | * | 65 ± 8 | 49 ± 5 | 1.3 ± 0.4 | 25 ± 6 |
| | 19 | 13 ± 2 | 2.5 ± 0.3 | * | 145 ± 28 | 88 ± 10 | 3.7 ± 0.6 | 23 ± 2 |
| | 20 | 6 ± 1 | 1.1 ± 0.1 | * | 55 ± 3 | 28 ± 1 | 1.65 ± 0.01 | 10 ± 3 |
| | 21 | 3 ± 1 | 0.6 ± 0.2 | * | 24 ± 9 | 18 ± 2 | 1.6 ± 0.1 | 11 ± 4 |
| | 22 | 9 ± 2 | 1.6 ± 0.3 | * | 91 ± 25 | 46 ± 9 | 3.3 ± 0.3 | 10.1 ± 0.4 |
| mean | | 8 ± 4 | 2 ± 1 | 214 ± 126 | 83 ± 49 | 60 ± 36 | 3 ± 1 | 15 ± 7 |

EXAMPLE 2

Rheological Characterization of the Sputa

The change of sputum viscoelasticity upon treatment with rhDNase I was determined with a controlled stress rotation rheometer (AR 1000 N, TA-Instruments, Brussels, Belgium) using a cone-plate geometry. The angle between the cone and the plate was 2 degrees and the sample volume required was approximately 0.9 ml. Dynamic oscillatory measurements were performed at a constant frequency of 1 Hz with a stress ranging from 0.01 to 0.1 Pa. In order to avoid disruption of the weak biopolymer network in the sputum due to the oscillation forces, the elastic modulus (G') and viscous modulus (G") of the sputum samples were determined in the linear viscoelastic region. All experiments were carried out at 20° C. in order to decrease the enzymatic degradation and dehydration of the sputum during the experiments (Sanders et al. in *J. Pharm. Sci.* (2000) 89:835-849). Sample dehydration was also prevented by using a solvent trap.

EXAMPLE 3

DNAse treatment of sputum

In order to evaluate the degradation of sputa by rhDNAse I, a 0.9 ml sputum fraction was taken from a sputum sample and the start value of its elasticity (G') and viscosity (G") was measured. Consequently, 86 μl rhDNAse I (126 μg/ml in 0.877% NaCl and 0.015% $CaCl_2$; (1 μg rhDNAse I=1 Genentech U)) was mixed with the sputum. The DNAse concentration in this experiment is in the range of the DNAse concentration measured in sputum of CF patients after administration of rhDNAse I (Pulmozyme®, Roche) (Sinicropi et al. in *Am. J. Respir. Crit. Care Med.* (1994) 149: A671). After 20 minutes incubation at 20° C., G' and G" of the sputum fraction was determined again. As a control 86 µl buffer was added to another 1.0 ml sputum fraction. Table 2 below shows the percent decrease in G' and G" due to cleavage of the sputum DNA by rhDNAse I. The net percentage decrease in viscoelasticity due to rhDNAse I was obtained by subtraction of the percent decrease caused by the excipient from the percent decrease caused by rhDNAse I and excipient. RhDNAse I was considered to be effective in decreasing sputum viscoelasticity in vitro when the percent decrease of both G' and G" was at least 10%. Ten of the thirteen sputa (i.e. 77%) obtained from CF patients who showed a clinical response on rhDNAse I were degraded in vitro by rhDNAse I. Seven of the nine sputa (i.e. 78%) obtained from CF patients who did not benefit from rhDNAse I therapy were also not degraded in vitro by rhDNAse I. Although a rather good correlation was observed between the effect of rhDNAse I in vitro and in vivo, using the effect of rhDNAse I on sputum viscoelasticity in vitro as a predictive parameter would result in a false prediction in about 25% of the cases.

TABLE 2

| | sputum sample | start value G' (Pa) | start value G" (Pa) | percent decrease G' (%) | percent decrease G" (%) |
|---|---|---|---|---|---|
| responder | 1 | 25 ± 7 | 6.5 ± 1.3 | 30 | 26 |
| | 2 | 5.3 ± 0.8 | 2.1 ± 0.3 | −2 | 0 |
| | 3 | 14 ± 6 | 4.3 ± 1.5 | 61 | 56 |
| | 4 | 3.0 ± 0.4 | 1.2 ± 0.1 | 80 | 33 |
| | 5 | 16 ± 4 | 4.2 ± 0.9 | 41 | 38 |
| | 6 | 3.4 ± 0.8 | 1.4 ± 0.2 | 9 | 7 |
| | 7 | 14 ± 4 | 3.3 ± 0.8 | 21 | 12 |
| | 8 | 6.6 ± 0.6 | 2.7 ± 0.3 | 35 | 30 |
| | 9 | 4.0 ± 0.1 | 1.5 ± 0.1 | 33 | 13 |
| | 10 | 2.8 ± 0.8 | 0.9 ± 0.1 | 7 | 11 |
| | 11 | 10 ± 1 | 2.8 ± 0.5 | 28 | 14 |
| | 12 | 2.1 ± 0.2 | 1.2 ± 0.2 | 33 | 17 |
| | 13 | 3.7 ± 0.4 | 1.6 ± 0.1 | 24 | 13 |
| Non-responder | 14 | 3.8 ± 0.7 | 1.4 ± 0.2 | 32 | 21 |
| | 15 | 17* | 4.0* | 29 | 23 |
| | 16 | 3.6 ± 0.1 | 1.5 ± 0.1 | 3 | 13 |
| | 17 | 11 ± 2 | 3.0 ± 0.5 | 0 | −7 |
| | 18 | 7 ± 1 | 2.2 ± 0.2 | 9 | 5 |
| | 19 | 2.5 ± 0.1 | 0.9 ± 0.1 | 4 | −11 |
| | 20 | 2.1 ± 0.3 | 1.0 ± 0.1 | 5 | 10 |
| | 21 | 6 ± 1 | 1.9 ± 0.4 | 8 | −5 |
| | 22 | 8 ± 2 | 2.1 ± 0.5 | 9 | 14 |

EXAMPLE 4

Effect of $K^+$ and $Mg^{2+}$ on DNAse Activity

The viscosity of DNA and DNA/actin solutions was measured with a calibrated capillary viscosimeter (Schott Geräte, Hofheim, Germany) equipped with an automated apparatus (Lauda, Köningshofen, Germany). The capillary viscosimeter was placed in a water bath (20.00° C.±0.05° C.) and the outflow times (t in s) were determined automatically. The viscosity ($\eta$) of the solutions is related to t by:

$$\eta = k\left(t - \frac{B}{t^2}\right)$$

where k and B are known constants. The effect of $Mg^{2+}$ and $K^+$ ions on the activity of DNAse (measured as decrease in viscosity) was determined by changing the $Mg^{2+}$ and $K^+$ concentration in a standardised DNA digest. DNA (salmon sperm DNA from Sigma) was digested (10 µl/ml rhDNAse I, 2,3 mg/ml DNA, 70 mM NaCl, and 3 mM $CaCl_2$, pH 7.0) in order to determine the change in viscosity of the DNA solution. Table 3 below shows that viscosity $\eta$ rapidly drops to a value near 1 $mm^2/s$ (i.e. the viscosity of water). This indicates that the administered amounts of $Mg^{2+}$ and $K^+$ do not interfere with the requirement of DNAse I for divalent cations.

TABLE 3

| DNA solution | $K^+$ (mM) | $Mg^{2+}$ (mM) | t = 0 min. $\eta$ ($mm^2/s$) | t = 10 minutes $\eta$ ($mm^2/s$) |
|---|---|---|---|---|
| 1 | 14.0 | 1.65 | 31.5 | 1.1 (97%) |
| 2 | 26.0 | 1.65 | 31.5 | 1.1 (97%) |
| 3 | 20.0 | 0.90 | 33.9 | 1.1 (97%) |
| 4 | 20.0 | 2.70 | 33.9 | 1.1 (97%) |

EXAMPLE 5

Influence of Actin Polymerisation on DNAse Activity

In a set-up comparable to example 4, the effect of $K^+$ and $Mg^{2+}$ on DNA degradation (decrease in viscosity) is measured in the presence of rabbit skeletal actin prepared according to Spudich et al. in *J. Biol. Chem.* (1971) 246: 4866-4871) (6,4 µg/ml rhDNAseI, 1.5 mg DNA/ml and 1.1 mg actin/ml 70 mM NaCl, 3 mM $CaCl_2$, 0.35 mM ATP, 3.2 mM TRIS/HCl, 0.13 mM DTT, and 0.006% $NaN_3$, pH 7,0). $K^+$ and $Mg^{2+}$ were supplied as $K_2HPO_4$ and $MgCl_2$ respectively. The viscosity of the DNA/actin solutions at different time points after the addition of rhDNase I are shown in table 4 below.

The DNAse activity is highest at high levels of $Mg^{2+}$ and $K^+$. This is in accordance with the fact that DNAse has a better performance when the F actin configuration is favoured under conditions of high ionic strength.

TABLE 4

| DNA/actin solution | $K^+$ (mM) | $Mg^{2+}$ (mM) | t = 0 min $\eta$ (mm2/s) | t = 10 min $\eta$ (mm2/s) | t = 20 min $\eta$ (mm2/s) | t = 30 min $\eta$ (mm2/s) |
|---|---|---|---|---|---|---|
| 1 | 14.0 | 0.90 | 14.3 | 9.8 (32%) | 9.4 (34%) | 8.6 (40%) |
| 2 | 26.0 | 0.90 | | | | 7.7 (46%) |
| 3 | 26.0 | 2.70 | | 6.1 (58%) | 5.8 (59%) | 5.5 (61%) |

The invention claimed is:

1. A method of treatment of a disease of the respiratory tract characterised by the presence of viscous mucus, said disease being cystic fibrosis, said method comprising administering to a patient in need thereof, a composition consisting essentially of a compound able to promote F actin formation, said compound being one or more selected from the group consisting of ionic forms of potassium and ionic forms of magnesium at a concentration of between 20 mM and 500 mM and between 20 mM and 100 mM, respectively, in combination with DNAse I, wherein said compound able to promote F actin formation improves the performance of said DNAse I in said viscous mucus.

2. The method according to claim 1, wherein said compound able to promote F actin formation is administered before, together or after said DNA degrading enzyme.

3. A method of treatment according to claim 1, wherein said compound is selected from potassium hydrogenphosphate ($KH_2PO_4$) and magnesium chloride ($MgCl_2$).

4. The method of claim 1, wherein said compound able to promote F actin formation by shifting the equilibrium between G actin and F actin is a magnesium salt.

5. The method of claim 1, wherein said compound able to promote F actin formation is an ionic form of potassium at a concentration of between 20 mM and 500 mM.

6. The method of claim 1, wherein said compound able to promote F actin formation is an ionic form of magnesium at a concentration of between 20 mM and 100 mM.

* * * * *